US00PP09575P

United States Patent [19]

Rühl

[11] Patent Number: Plant 9,575

[45] Date of Patent: Jun. 11, 1996

[54] 'BORNER' ROOTSTOCK GRAPE

[76] Inventor: Ernst H. Rühl, Eibingeweg 1, D-65366 Geisenheim, Germany

[21] Appl. No.: 350,881

[22] Filed: Nov. 29, 1994

[51] Int. Cl.[6] ..... A01H 5/00

[52] U.S. Cl. ..... Plt./47.1

[58] Field of Search ..... Plt./47.1, 47.2, Plt./47.3

[56] References Cited

U.S. PATENT DOCUMENTS

P.P. 6,166 5/1988 Lider et al. ..... Plt./47.1

P.P. 6,319 10/1988 Lider et al. ..... Plt./47.1

*Primary Examiner*—James R. Feyrer

*Attorney, Agent, or Firm*—Richard C. Litman

[57] ABSTRACT

Rootstock variety 'Börner' is a cross between *Vitis riparia* 183G×*Vitis cinerea* Arnold. The new variety was obtained by traditional grapevine crossbreeding techniques. The basic idea for the choice of the two breeding partners was to combine the positive viticultural characteristics of *Vitis riparia* with the complete phylloxera resistance potential of *Vitis cinerea.*

2 Drawing Sheets

BACKGROUND OF THE INVENTION

The problem of Phylloxera has been remedied by the present invention. Phylloxera is a louse of the genus Phylloxera that attacks plants by sucking sap and related material from roots, leaves, etc. One type of phylloxera, *P. vitifoliae* (grape phylloxera), destroys the leaves and roots of grapevines throughout North America and Europe. Historically, Phylloxera has been documented as a major threat to viticulture around the world, having wiped out viticulture in large areas of Europe during the second half of the 19th century.

At the beginning of the 20th century, the German research scientist Carl Börner observed that one type of *Vitis cinerea* (*Vitis cinerea* Arnold) was not only tolerant, but actually resistant to phylloxera. *Vitis cinerea* did not permit the insect to feed on its roots. Unfortunately, *Vitis cinerea* Arnold has poor rooting and grafting ability. Thus, although genetically superior, *Vitis cinerea* Arnold never found its place as a rootstock variety.

Yearning for a rootstock variety that has high phylloxera resistance and excellent grafting and rooting ability, Börner conducted a large number of crosses between *Vitis cinerea* Arnold and other varieties and species. The seedlings were grown in several seedling fields throughout Germany.

In 1936, an initial crossing was conducted at the former "Biologische Reichsanstalt" in Naumburg/Saale during a huge rootstock breeding program that was carried out with the aim of total elimination of Phylloxera. The seedlings which resulted from this breeding program were planted in 1943, by the "Reichsrebenzüchtung" on an examination field in the Zellertal in the Palatinate area, which belonged to the "Landes—Lehr—und Forschungsanstalt Neustadt an der Weinstrasse." Remarkably, the plants survived the Holocaust and World War II.

In 1964, a special selection of the most interesting and most promising new rootstocks derived from the Zellertal were taken to the "Forschungsanstalt Geisenhem/Institut f ür Rebenzüchtung." At Geisenheim, Helmut Becker continued Börner's research and examined a range of seedlings more closely. Dr. Ernst Rühl, as the director at Geisenheim, originally supervised and directed the selection and asexual reproduction of the 'Börner'. Dr. Becker was amongst those so directed. The name 'Borner' is an attribute to the original sexually reproduced crosses between *Vitis cinerea* Arnold and other varieties and species, performed by Carl Börner. From the special selection, one new variety was eventually chosen for its strikingly positive viticultural characteristics and its complete phylloxera resistance. The new variety—Selection number Na 5153-54, a cross between *Vitis riparia* 183 Geisenheim and *Vitis cinerea* Arnold—proved to combine the complete phylloxera resistance of *Vitis cinerea* Arnold with the good rooting and grafting ability of *Vitis riparia.*

Numerous adaptaton, affinity, and resistance tests in various experimental vineyards and under commercial conditions proved positive. Both studies and rootstock trials in several areas under a range of conditions have since shown the positive effect of this rootstock on the performance of the scion and its superiority under high Phylloxera pressure. Thus, the 'Börner' variety represents a phylloxera-tolerant rootstock, possessing the ability to retain root system integrity after phylloxera attack, and it has exceptional rooting and grafting ability. variety represents Several 'Börner' motherblocks have been established in Germany, Northern Italy, South France, and Central Portugal. The stock plantations produce propagation material or rootstocks for grafting or any other purpose. Maintenance of the variety is achieved by clonal selection of the original motherplants in combination with negative mass selection in special motherblocks. The variety is maintained by controlled production of pre-base (elite) and base rooted cuttings used for the establishment of new other rootstock propagation plantations for the production of rootstocks for grapevine grafting. Asexual reproduction of the 'Börner' is and has always been executed under the strict and accurate control of Ernst Rühl. Whether asexual reproduction is carried out in Geisenheim's own nursery at Geisenheim/Rheingau, Germany, or in specially selected private nurseries under particular contractual conditions specified for the production of rooted rootstocks, selected and controlled base and pre-base material are always utilized. The 'Borner' has displayed stability under asexual reproduction.

In 1989, the 'Börner' was registered in the German Variety Registration Office. The National Plant Variety Catalogue of Germany listed the 'Börner' with registration number RBU 15. No other synonyms for the 'Börner' have been utilized separate from 'Börner', Na 5153-54, and RBU 15. In 1991, the 'Börner' was classified in the European Community for all German vine-growing regions. Trials in Italy, Austria, Slovenia, France and other European countries are pending.

SUMMARY OF THE INVENTION

The present invention relates to a new and improved grapevine rootstock variety, having proved high resistance against Phylloxera and effective tolerance against the transmission of grapevine fanleaf virus by nematode vectors like *Xiphinema index.* Rooting and grafting ability resembles that of the Berlandieri×Riperia group.

BRIEF DESCRIPTION OF THE DRAWINGS

FIG. 3 typifies the lower side of a mature leaf of the new variety.

FIG. 4 shows the flowers of the new variety.

BOTANICAL DESCRIPTION OF THE PLANT

Figure 1:
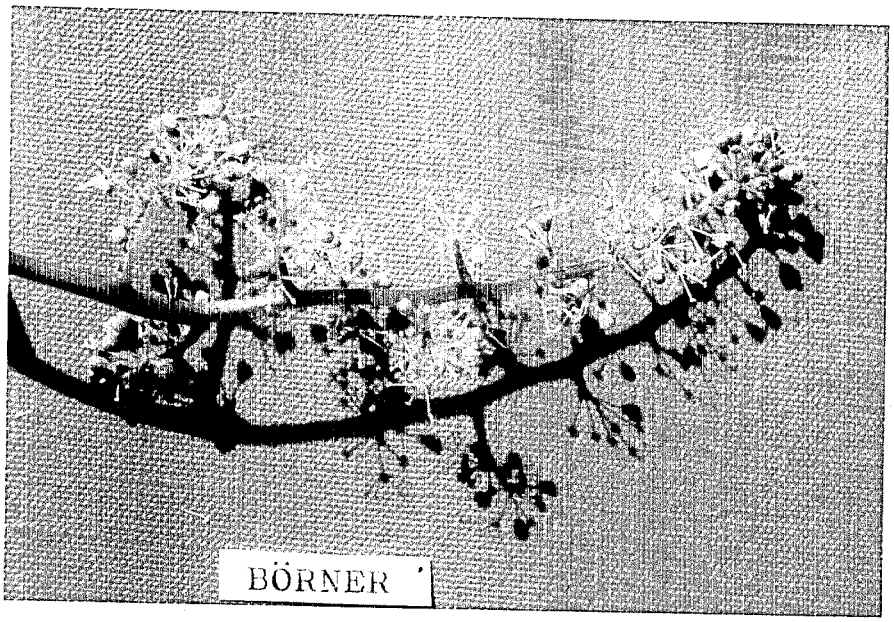
FIG. 1 shows a typical flower cluster of the new variety.
Figure 2:
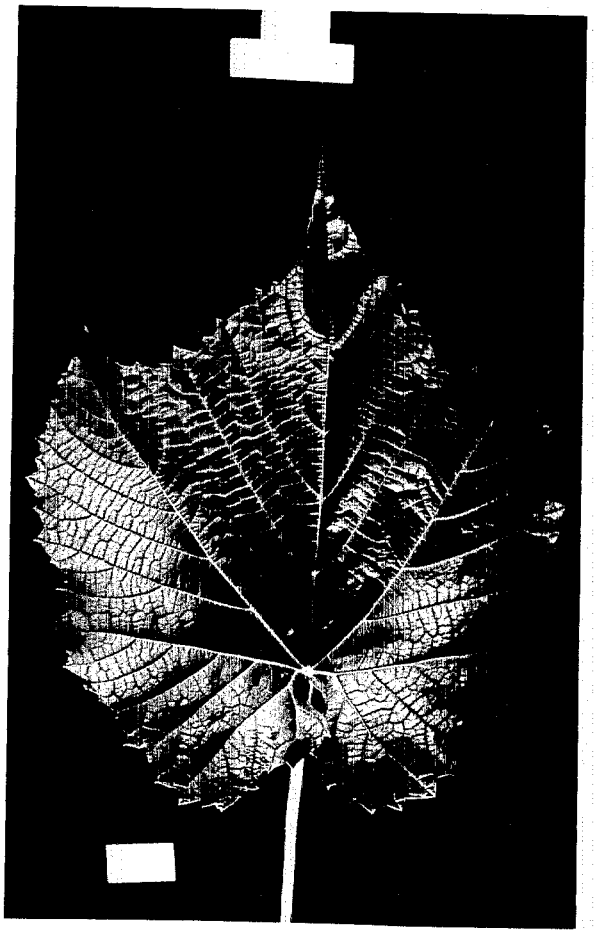
FIG. 2 typifies the upper side of a mature leaf of the new variety.

The 'Börner' partially presents ampelographic similarities to *Vitis cinerea,* such as growing tip and leaf form characteristics, but it is distinct in earlier wood ripening and better rooting. The coloration of various plant parts is not seen to lie outside the normal range for either parent species.

Definitive phenological and morphological characteristics of the 'Börner' rootstock are as follows:

Growth: Early bud break with medium to strong growth and medium growth of laterals. Under the climatic conditions of the Rheingau area, the 'Börner' produces 50–70 graftable rootstock cuttings of 0.40 cm length with a diameter of 0.07–0.11 m per year when 6–8 shoots per plant are pruned, and achieves mature wood of 4.00 m per shoot when rooted at Geisenheim/Rheingau, Germany.

Soil adaptability: Good adaptability to most soils for grape growing. Moderately susceptible for alkaline soils.

Dormancy: Medium–late.

Resistance: Resistant against the Fungi *Plasmopora viticola, Uncinula necator* and *Botrytis cinerea.* 100% resistant against the root louise phylloxera. The phylloxera cannot form any galls or lesions on the roots or leaves. The root and leaf tissue shows a necrotic reaction after the phylloxera attack. In specific laboratory and field tests, the 'Börner' has been shown to effectively tolerate varius vectors of the *Xiphinema index* nematode complex. Under field conditions, it showed tolerance also to *Longidorus attenuatus.*

Affinity: Anatomical and physiological compatibility with its grafting partner to guarantee growth, grape production and grape quality. Testing and practical experience show a very good graft compatability with 'Chardonnay', 'Riesling', 'Muller-Thurgau', 'Gerwurztraminer', 'Ehrenfelser', 'Slivaner', 'Kerner', 'Elbling', 'Pinot Blanc', 'Pinot Gris', 'Pinot Noir', 'Pinot Noir Precoce', 'Dunkelfelder', 'Lim erger', 'St. Laurent', 'Auxerrois', 'Portugieser', 'Trollinger', 'Dornfelder', and many more Vines grafted on the rootstock 'Borner' have never shown any differences of vigor and productivity in comparison to other rootstock combinations, e.g. SO 4, 5 C, 5 BB, 125 AA. In special adaptation trial vineyards it showed a higher tolerance to drought than all other rootstock varieties.

Young shoot: Tip is half-opened (half enclosed by small leaves) with a strong intensity of striped anthocyanin coloration, extremely dense prostrate hairs, and sparse to medium dense erect hairs.

Shoot: Dorsal sides of internodes and nodes are green, ventral sides of internodes are green with red stripes, and ventral sides of nodes are red. Erect hairs on nodes and internodes are medium to dense. Shoots have medium anthocyanin coloration and are semi-erect to horizontal in attitude.

Woody shoot: Elliptic cross-secton, striated surface with medium to dark brown main color and reddish brown stripes, lenticels absent, dense to very dense erect hairs on nodes and internodes, early bud burst. Internode length from 0.21 m to 0.28 m, cane thickness from 0.06–0.14 m.

Tendrils: Distributed discontinuously on the shoot (2R-O-2R, 3-branched, wine-red color, length 0.24–0.37 m, few single woody hairs, sparse to medium dense erect hairs on the basis.

Yount leaf: Upper side is copper-yellow to yellow, medium intensity of anthocyanin coloration. Between veins, prostrate hairs are dense to very dense and erect hairs are of sparse to medium density. On main veins, sparse density of prostrate hairs and dense distribution of erect hairs.

Mature leaf: Blade is 21–23 cm long, cordate shaped, zero to three lobes, dark green upper side, flat profile. Weak blistering on upper side of blade, no undulation of blade between main and lateral veins, rectilinear short to medium teeth. Petiole sinus slightly open, closed, and lobes slightly overlapping. Base of petiole sinus is V-shaped. Anthocyanin coloration of main veins is weak to medium on the upper side of the blade, and absent or very weak to weak on the lower side of the blade. On the lower side of the blade between the veins, prostrate hairs have strong density while erect hairs have very sparse or no density. On main veins on the lower side, prostrate hairs are sparse while erect hairs are medium to dense in concentration. The petiole is at least 17 cm long. On the petiole, prostrate hairs are of sparse to medium density and erect hairs are very dense in concentration.

Flower: Male flower with medium-sized flower cluster, consistently with six anthers, pistils only occasionally and in very slight vetigial form, length 0.16 m–0.21 m, fertile pollen with light yellow color, each flower cluster produces about 0.5–0.7 g of pollen

I claim:

1. The new and distinct variety of grapevine rootstock herein described and illustrated and identified by the characteristics enumerated above.

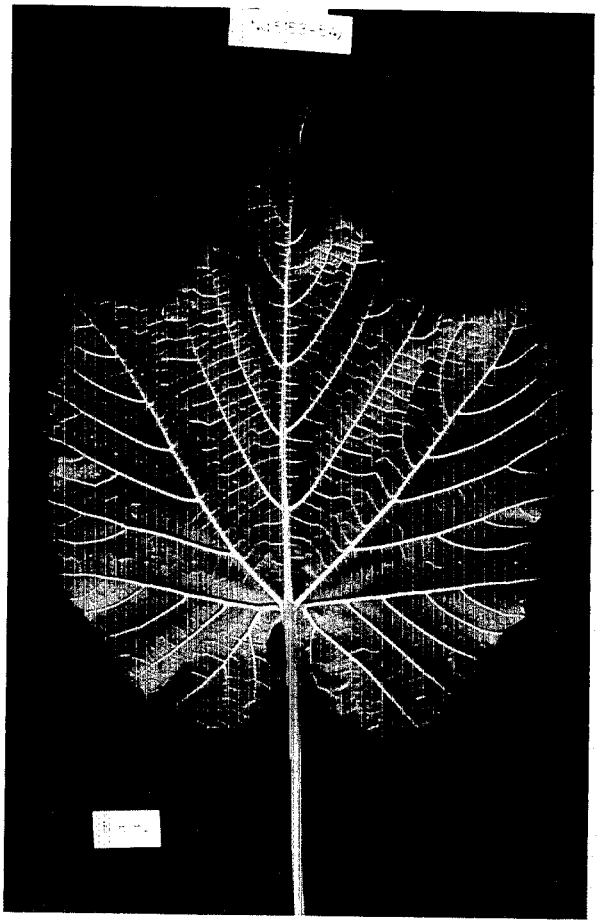
Fig. 3
Fig. 4
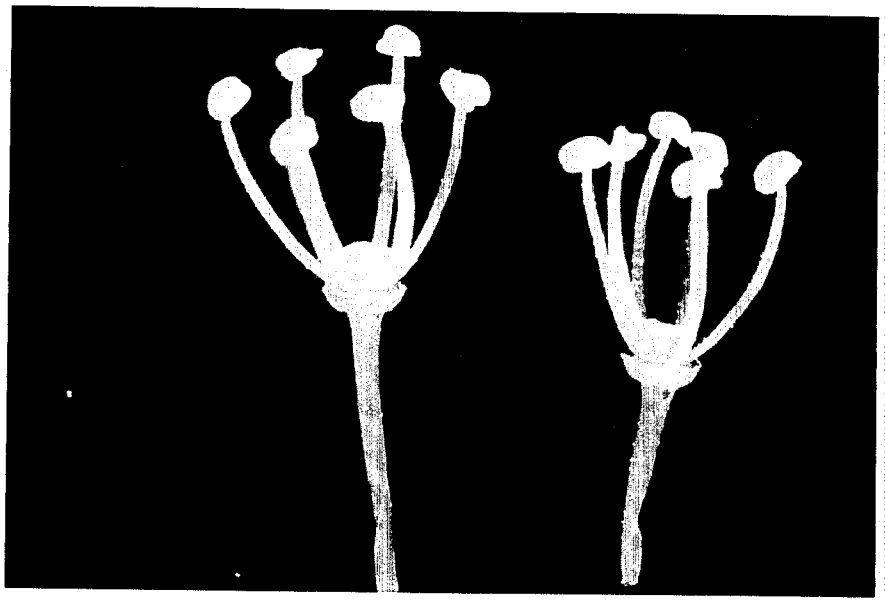

* * * * *